(12) United States Patent
Sohmer et al.

(10) Patent No.: US 6,832,110 B2
(45) Date of Patent: Dec. 14, 2004

(54) METHOD FOR ANALYSIS OF ONGOING AND EVOKED NEURO-ELECTRICAL ACTIVITY

(76) Inventors: Haim Sohmer, 37 Shachal Street, Jerusalem (IL), 93702; Vladimir Rodionov, P.O. Box 647, Bet Shemesh (IL), 99000; Craig Goodman, 63 Diezengoff Street, Netanya (IL), 42438

( * ) Notice: Subject to any disclaimer, the term of this patent is extended or adjusted under 35 U.S.C. 154(b) by 271 days.

(21) Appl. No.: 10/235,163

(22) Filed: Sep. 5, 2002

(65) Prior Publication Data

US 2003/0073921 A1 Apr. 17, 2003

Related U.S. Application Data

(60) Provisional application No. 60/316,974, filed on Sep. 5, 2001.

(51) Int. Cl.$^7$ .................................................. A61B 5/00
(52) U.S. Cl. ...................................................... 600/544
(58) Field of Search .................................. 600/544–545

(56) References Cited

U.S. PATENT DOCUMENTS

| | | | |
|---|---|---|---|
| 3,901,215 A | * | 8/1975 | John ........................... 600/544 |
| 4,493,327 A | * | 1/1985 | Bergelson et al. ........... 600/544 |
| 4,672,978 A | * | 6/1987 | Danto ......................... 600/595 |
| 5,392,788 A | * | 2/1995 | Hudspeth ..................... 600/544 |
| 6,067,467 A | * | 5/2000 | John ........................... 600/544 |

* cited by examiner

Primary Examiner—Robert L. Nasser
(74) Attorney, Agent, or Firm—Scully, Scott Murphy & Presser (57) ABSTRACT

A method of analyzing EEG and EP data in order to differentiate between ongoing neuro-electric activity of the brain of a subject and evoked neuro-electric activity of the brain of the subject, the analysis being based upon the frequency and the amplitude of deflections from the base line of the EEG and EP data, the method including a. recording by EEG measurement the ongoing neuro-electric activity; b. administering a series of sensory stimuli to the subject; c. recording by EEG and EP measurement neuro-electric activity evoked in response to the stimuli; d. marking the time of occurrence, polarity and amplitude of each of the deflections recorded; e. generating a histogram of time periods of the deflections for a defined duration prior to, during and subsequent to each of the single stimuli, the histogram reflecting the deflections within the time periods, generating a deflection time distribution based upon data from the histogram, generating an amplitude profile of the deflections, and f using the deflection time distribution and the amplitude profile to statistically analyze and evaluate the ongoing and evoked neuro-electric activity; such that the differentiation between the ongoing and the evoked neuro-electric activity may be quantified.

19 Claims, 9 Drawing Sheets

Step 1 — Recording neuro-electric activity by EEG

Step 2 — Administering stimuli

Step 3 — Recording neuro-electric activity by EEG

Step 4 — Marking parameters of deflections, generating histogram of time periods, generating deflection time distribution, generating amplitude profile, generating algorithm

METHOD FOR ANALYSIS OF ONGOING AND EVOKED NEURO-ELECTRICAL ACTIVITY

CROSS REFERENCE TO RELATED APPLICATIONS

The present application claims benefit of U.S. Provisional Application No. 60/316,974 filed Sep. 5, 2001.

FIELD AND BACKGROUND OF THE INVENTION

The present invention relates to the field of measurement and analysis of brain function and, more particularly, to a method of analysis of EEG and evoked potential (EP) generated data which allows differentiation between ongoing cortical neuro-electric activity and evoked cortical neuro-electric activity of a subject.

The conventional analysis of EPs is based on averaged data due to the small signal (response) to noise (background EEG) ratio. Thus, data concerning individual trials and the variation of the evoked responses from trial to trial are lost and the nature of the individual response is unclear. For example, a typical goal in EP analysis in clinical cases is to elucidate the reason for the attenuation of particular EP components: is it due to variations in latency of the components across trials or to lower amplitudes of that component in several individual trials? Therefore, many studies have searched for a technique which could possibly provide single trial analysis of the evoked responses An alternative approach is based on the assumption that the waveform of the conventionally averaged EP is similar to that of the single response so that the averaged response can be used as a criteria (template) for the selection of the appropriate trials for single trial analysis. Thus, only the components of EP which are obtained after averaging can then be used in this approach. However, it is known that some single trial components can be distorted, highly decreased in amplitude or even lost as a result of the averaging, leading to a loss of possibly important information needed for such a study of single trial responses.

The frequency analysis technique has also been suggested to study the evoked potentials in single trials. Thus the evoked potentials can be considered to result from a reorganization of the phases of the ongoing EEG or from selective amplification of EEG in specific frequency bands. However, these spectral (frequency domain) methods do not relate to the local time properties of the responses (e.g. latencies of the particular EP components), and the methods do not allow study of the local time variations of the EP.

Recent studies have shown that background activity and single trial responses are integrated with each other. Consequently it would be advantageous to use the same method for processing and analyzing both aspects (responses and background) of the recorded activity. However, the problem of differentiation of single trial evoked responses from the background EEG activity has yet to be solved, and reliable methods for the analysis of EP and background variability are needed.

There is thus a widely recognized need for a method of EEG and EP data analysis that is devoid of the above described limitations and that facilitates the differentiation of the ongoing cortical neuro-electric activity and the evoked cortical neuro-electric activity of the brain of a subject.

SUMMARY OF THE INVENTION

Accordingly, it is an object of the present invention to provide a method of EEG and EP data analysis that facilitates the differentiation of the ongoing cortical neuro-electric activity and the evoked cortical neuro-electric activity of the brain of a subject.

It is a further object of the present invention to provide a method that may identify responses to single stimuli evoking neuro-electrical activity.

It is a further object of the present invention to provide a method that may be actuated by an algorithm.

It is a further object of the present invention to provide a method that employs an algorithm that is computer programmable.

It is a further object of the present invention to provide a method that employs an algorithm that may be modified to provide for analysis of differing EEG and EP data.

The present invention describes a novel method for the analysis of both the neural electrical activity initiated in response to a series of sensory stimuli and of ongoing neural electrical activity. The positive and negative deflections in the EEG activity are detected and the time distributions and the amplitude as a function of time distributions of these deflections are obtained. This provides a statistical description of the appearance of positive and negative deflections or fluctuations in the ongoing EEG before, during and after a series of sensory stimuli. An algorithm based upon the statistical description is used to quantify the differentiation between the neural electrical activity evoked by the stimuli and the background EEG, both with respect to the number of these deflections and with respect to their amplitude. This differentiation provides insights into the possible relations between evoked and background EEG activity, leading to a better understanding of how evoked potentials are generated.

Accordingly, there is provided a method of analyzing EEG and EP data in order to differentiate between ongoing neuro-electric activity of the brain of a subject and evoked neuro-electric activity of the brain of the subject, the analysis being based upon the frequency and the amplitude of deflections from the base line of the EEG and EP data, the method comprising a. recording by EEG measurement the ongoing neuro-electric activity; b. administering a series of sensory stimuli to the subject; c. recording by EEG and EP measurement neuro-electric activity evoked in response to the stimuli; d. marking the time of occurrence, polarity and amplitude of each of the deflections recorded; e. generating a histogram of time periods of the deflections for a defined duration prior to, during and subsequent to each of the single stimuli, the histogram reflecting the deflections within the time periods, generating a deflection time distribution based upon data from the histogram, generating an amplitude profile of the deflections; and f using the deflection time distribution and the amplitude profile to statistically analyze and evaluate the ongoing and evoked neuro-electric activity; such that the differentiation between the ongoing and the evoked neuro-electric activity may be quantified.

BRIEF DESCRIPTION OF THE DRAWINGS

With specific reference now to the drawings in detail, it is stressed that the particulars shown are by way of example and for the purposes of illustrative discussion of the preferred embodiment of the present invention only, and are presented in the cause of providing what is believed to be the most useful and readily understood description of the principles and conceptual aspects of the invention. In this regard, no attempt is made to show details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of a method of EEG and EP analysis which preserves the moment-to-moment variation in scalp recorded activity, helps differentiate between evoked and ongoing electrical activity and provides a constructive basis for the study of the single evoked responses. Moreover, the variability of the responses can be evaluated by this method.

Figure 1:
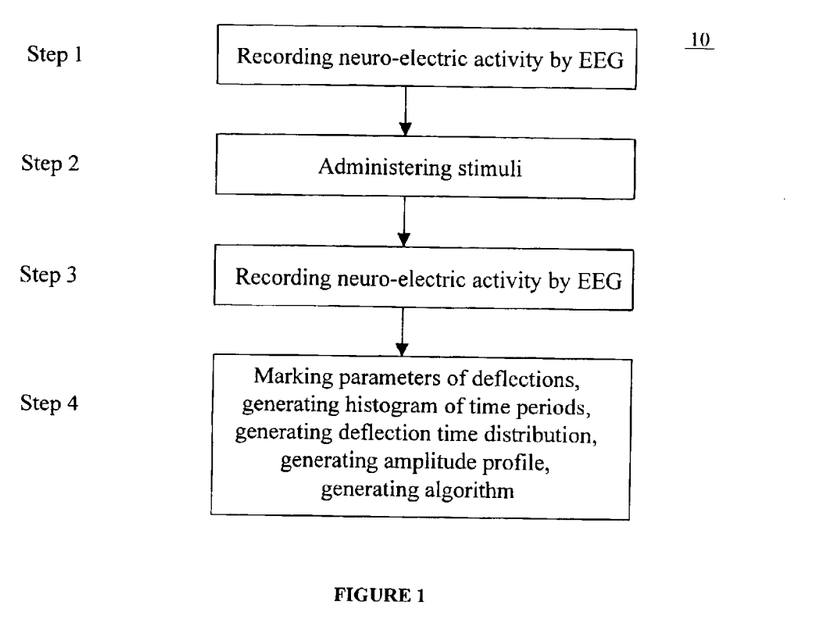
FIG. 1 is a flow chart illustrating the method provided in accordance with the present invention.

Reference is now made to FIG. 1 which shows a flow chart illustrating a method of analysis of EEG and EP data according to the teachings of the present invention, which is referred to hereinbelow as method 10.

Step 1 consists of recording ongoing neuro-electric activity within the frequency range of interest of a subject by common equipment at the subject's scalp using a set of electroencephalograph electrodes and amplifier and analog/digital(A/D) converters to provide a set of digital data representing the subject's neuro-electric activity prior to the provision of stimuli. The duration of the measurement may vary according to the quantity of data and degree of precision of differentiation desired.

Step 2 consists of administering a series of sensory stimuli to said subject. The stimuli may consist of any sensory stimulus, including but not limited to visual, auditory, tactile, gustatory or olfactory and/or may include performing an attention demanding task or engaging the memory process or other cognitive tasks. It is appreciated that the nature of the stimulus is not a material element of the invention and the method of the present invention may be employed with respect to any stimulus that evokes neuro-electrical activity.

Step 3 consists of recording the neuro-electric activity evoked in response to the stimuli. The measurement is taken as described with respect to step 1 above.

Steps 4 through 8 are best illustrated by example and are therefore described more fully hereinafter with respect to the study set forth hereinafter. Such steps include the following:

Step 4 consists of marking the time of occurrence, polarity and amplitude of each of the deflections recorded by the EEG device. The deflections may be both positive and negative deflections from the baseline of the EEG data.

Step 5 consists of generating a histogram of time periods of the deflections for a defined duration prior to, during and subsequent to each stimulus. The histogram will reflect the deflections within time periods ranging from 3 to 10 ms and preferably 6 ms. Said time periods may vary in duration as desired by the Examiner, depending on the frequency range of EEG to be analyzed. The histogram may span any time period desired by the examiner, for example a duration of 1300 ms, 300 ms prior to the stimulus and 1000 ms after the stimulus.

Step 6 consists of generating a deflection time distribution based upon data from the histogram.

Step 7 consists of generating an amplitude profile of the deflections.

Step 8 consists of using the deflection time distribution and the amplitude profile along with statistical procedures to evaluate the ongoing and the evoked neuro-electric activity by assigning a value to each time period.

The statistical procedures can be modified to take into account all frequency bands of recorded brain electrical activity. As described in the following study, synchronization of the alpha-beta frequency deflections with onset of the stimulus seems to be limited to latencies up to 200 ms., while later components (e.g. P300) might be generated by EEG waves lower in frequency content. It is understood that the algorithm may preferably be modifiable to allow analysis of evoked neuro-electric activity of different frequencies and amplitudes, including shorter and longer latency evoked responses and lower and higher frequency deflections.

The analysis may be used for examining the timing of the neuro-electric activity, the variability of the neuro-electric activity and the correlation of the neuro-electric activity and therefore may also be helpful in identifying and/or analyzing the stimuli evoking the neuro-electric activity. The algorithm is preferably actuatable by a computer and, like all modern EEG measurement algorithms, is capable of being programmed.

Method 10 may be used for all customary purposes carried out or facilitated by EEG and EP examination, including but not limited to measuring the effect of a stimulus on a subject compared to the effect of the stimulus on other subjects, measuring the effect of a stimulus on a subject over a period of time, measuring the effect of medicine or anesthesia on a response of a subject to a stimulus, measuring the effectiveness of a remedial program on a response of a subject to a stimulus, measuring the effect of fatigue on a response of a subject to a stimulus, measuring the effect of injury or disease on a response of a subject to a stimulus and measuring the effect of recovery from injury or disease on a response of a subject to a stimulus. Method 10 may also be useful for evaluating a subject's level of alertness, mental efforts and brain utilization, sustained focused attention, neurocognitive strategy, cognitive speed, transient focused attention, response to changes in mental workload and quickness to adapt.

Additional objects, advantages, and novel features of the present invention will become apparent to one ordinarily skilled in the art upon examination of the following study, which is not intended to be limiting. Additionally, each of the various aspects of the present invention as delineated herein and/or as claimed in the claims section below finds experimental support in the following study.

Subjects

Fourteen male subjects (age range 18–30 years) were invited to participate in the study as paid participants. All subjects had normal vision (in some cases corrected with glasses) and normal hearing.

Stimuli

Auditory and visual stimuli were presented in alternating order at an overall rate of 1/sec. The duration of a stimulation/recording session was 600 sec (300 auditory and 300 visual stimuli: Aud-Vis-Aud-Vis . . . ). Six sessions on two experimental days (three sessions per day) were conducted with each subject. To insure subject attentiveness, the subject was instructed to perform mental counting of each perceived auditory stimulus. The auditory stimulus was a binaural click of 30 dB above the subject's subjective threshold (i.e. SL). The visual stimulus consisted of an alternating checkerboard with fill field of 11° (25.7 cm.) and the angle for check viewing of 1.35° (a rather low basic spatial frequency of visual stimuli). Subjects were sitting 140 cm. from a 27×21 cm. CTX computer screen, which provided the visual stimuli. In 3 of these subjects a session was conducted during which stimuli were not presented. This report describes the analysis of the responses to the visual stimuli only.

Apparatus and Procedure

Scalp activity was recorded with an Electrocap (Neuroscan, Inc., U.S.A.) using sixteen monopolar electrode sites: Fz, F3, F4, Cz, C3, C4, T3, T4, T5, T6, Pz, P3, P4, O1, O2, and Oz of the international 10–20 electrode placement system with the reference electrode at the mastoid, and the ground electrode was located on the forehead. Vertical and horizontal electrooculograms (EOGs) were recorded in order to control for eye movement artifacts. The stimulus presentations and data acquisition were provided by a STIM/SCAN EEG/EP workstation (Neuroscan, Inc., U.S.A.). EEG and EOG channels were continuously recorded through Synamps Amplifiers (bandpass=0.1 to 100 Hz) and digitized at a rate of 1000 Hz. Data were stored and analyzed off line.

Data Processing

The 1,300 ms EEG segment recorded, beginning at 300 ms before the visual stimulus and continuing 1000 ms after stimulus presentation was defined as a single trial. The frequency content of the recorded activity was limited by the bandpass filter used (1–30 Hz). In addition, smoothing of traces was conducted across every 5 data points. Eye movement artifact reduction was performed for all data using a NeuroScan procedure on the basis of the vertical electrooculogram (VEOG). Computer algorithms were used to identify the positive and negative deflections and the time of their peaks (FIG. 2) during the 300 ms pre-stimulus and the 1,000 ms post-stimulus period. The base to peak amplitude of each such deflection was also measured (FIG. 3).

Figure 2:
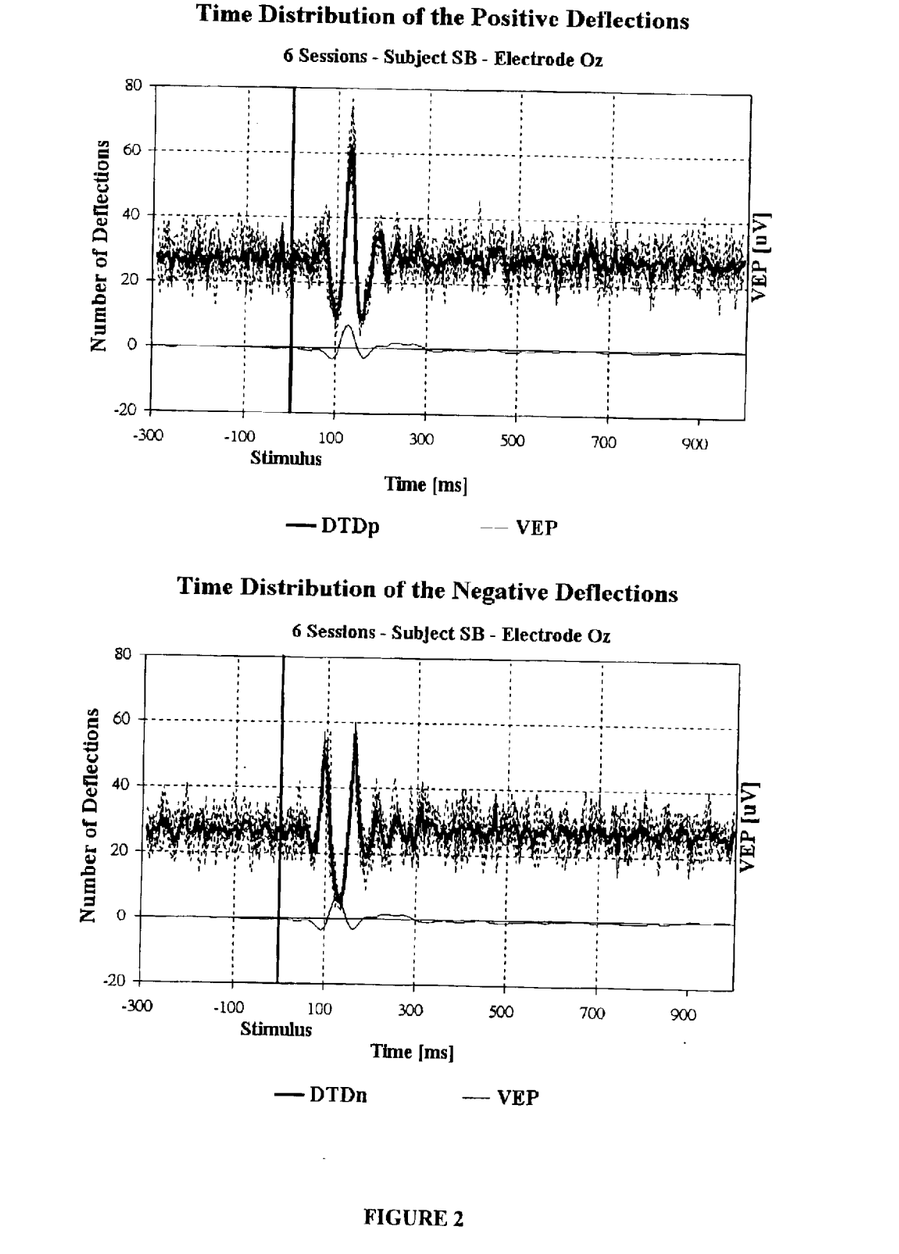
FIGS. 2 to 10 are graphic representations of data relevant to a described study of the implementation of the method of FIG. 1.

The time coordinates of the deflections with respect to the onset of the stimulus trigger were determined separately for positive and negative deflections for each trial. Thus each single trial could be described by a sequence of events (deflections), each of which had a time coordinate (with respect to the stimulus), polarity and amplitude. The number of positive and negative deflections in bins of 6 ms each calculated for a series of up to 300 trials was defined as "Deflection Time Distribution" for the given subject, given number of trials and given session (FIG. 2). The Deflection Time Distributions obtained over the six different recording sessions from the same subject could be combined (averaged or summated, wherever appropriate) into a composite Deflection Time Distributions. Deflection time distributions of the times of the positive and negative (separately) deflections were obtained for each subject.

Figure 3:
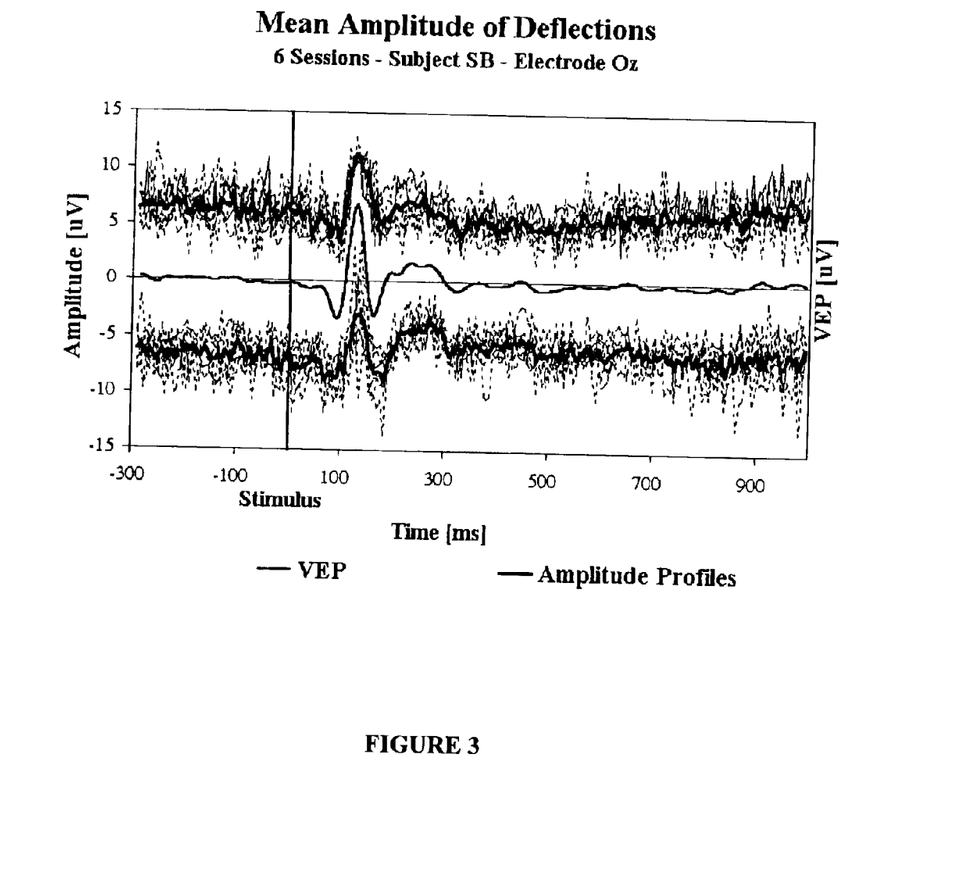

In addition, the amplitudes (base to peak) of the same deflections within each time bin as a function of post stimulus time could be used for the calculation of the Amplitude Profile for up to 300 trials over six sessions for each subject (FIG. 3). In general all 300 trials from a single session were combined into an Amplitude Profile. These deflection time distributions and amplitude profiles were the basis for further analysis which included, for example, statistical evaluation of the proportion of positive and negative deflections and their amplitudes in specific time periods with respect to the stimulus and analysis of the sequence of positive and then negative deflections and vice versa, in relation to the stimulus.

These same data were also subjected to conventional averaging and the deflection time distributions and the Amplitude Profiles obtained with this new technique were compared to the conventionally averaged EPs obtained from the same subjects, from the same recording sites over the same time period and for the same components. The latency of conventionally averaged VEP P1 components was identified as the most positive point between 75 and 135 ms, N1 as the most negative point between 55 and 95 ms, and N2 as the most negative point between 130 and 206 ms.

The EEG recorded in three of the same subjects in the sessions without sensory stimuli was analyzed with the new technique in order to specify the time and amplitude distributions of true background activity. This would help in evaluating the time period which is truly "response" in nature.

Results

1. Differentiation Between Background and Evoked Activity on the Basis of the Deflection Time Distributions Inspection of the time and amplitude distributions of the deflections as a function of time in a typical subject over all 6 recording sessions (FIG. 2) reveals that during the 300 ms prestimulus period and from about 400 ms after the stimulus (time 0), there are no major peaks. This indicates that during these periods, the number of deflections is at a uniform low level and that their amplitude is relatively constant, reflecting background activity. On the other hand, inspection of time and amplitude distribution of the deflections during the period from the stimulus up to about 400 ms after the stimulus (FIGS. 2, 3) reveals several time periods with clear increases in the number of positive and negative deflections and peaks in the amplitude profiles. This obviously represents the stimulus evoked activity reflected in these distributions.

In order to quantitatively determine the time periods during which only background (not time-locked) activity was present, the 300 ms of prestimulus time and 300 ms of late poststimulus time (interval 700–1000 ms) in the deflection time and amplitude distributions were compared. Similar distributions of uniform low level of number and amplitude of deflections were obtained in these two time intervals. In addition, similar uniform distributions were obtained in three subjects when the recordings were also conducted in the absence of any sensory stimuli. This helps define the 300 ms prestimulus period and the 300 ms (700–1000 ms) period post stimulus as the stationary (background) activity.

In order to define a statistical criteria for the presence of an evoked response, one must first define the variance of the background activity for the time period described above. An evoked response will then be indicated by a significant increase in this variance above some critical level.

One may assume that the difference between the number of positive and negative deflections in the time bins representing the background activity across trials would be small and differ only by chance from zero, i.e. the probabilities of detecting positive or negative deflections in the particular time bins (across trials) would be equal. In order to obtain a statistical measure of this variance between the number of positive and negative deflections which would help differentiate between background and evoked activity, a parameter R was defined as the normalized difference between the numbers of positive and negative deflections obtained in the particular time bin over the set of trials:

$$R = (\#p - \#n)/\text{SQRT}(\#p + \#n), \tag{1}$$

where $\#p$—number of positive deflections obtained in particular time bin,—obtained from Positive Deflection Time Distribution;

n—number of negative deflections obtained in particular time bin,—obtained from Negative Deflection Time Distribution;

SQRT—square root.

The R value would be distributed approximately as a standard normal variance N(0,1) if the probability to obtain positive deflections in the given time bin over N trials is equal to the probability of obtaining negative deflections (i.e. background activity).

Figure 4:
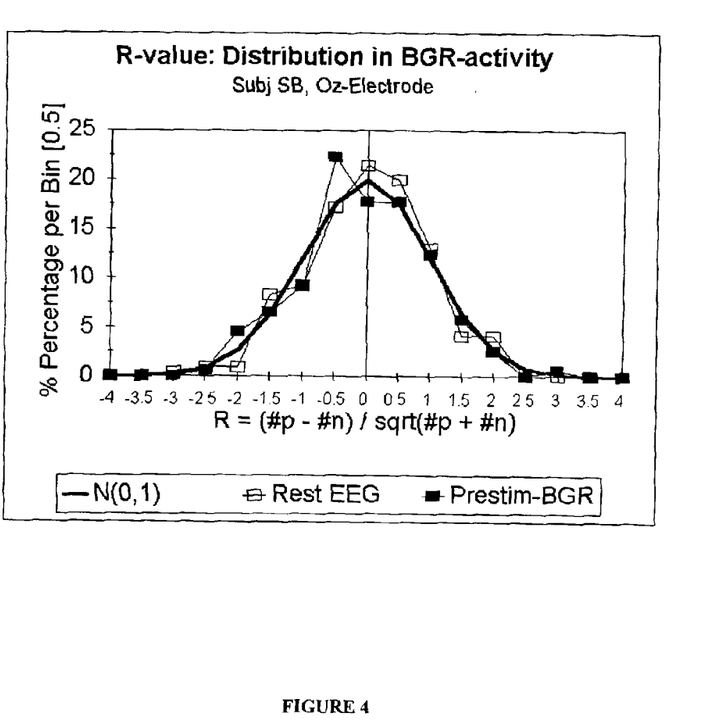

FIG. 4 shows the R-values obtained during the resting EEG (absence of stimulus) and in the prestimulus intervals in subject SB, along with the distribution N(0,1) superimposed. This figure illustrates that the experimental data during background activity is in agreement with a standard normal variance distribution.

Entering the values of R obtained during background activity into the table of normal (Gauss) distribution N(0,1) provides the criterion for assessing the presence of an R value significantly greater than that during background activity (which would then be evoked activity). However, one has to keep in mind that the critical level $R_{cr}$ (p<0.05) is dependent on the duration of the time interval of the analysis, since higher values of R are more probable during longer samples of background activity. Thus a stronger criteria for the detection of a significant deviation of R must be applied during longer time intervals. For example, a duration of 1300 ms (216 time bins of 6 ms) requires a critical level $R_{cr}$ (p<0.05)=3.5. However, for 100 ms poststimulus time (only 16 time bins of 6 ms), the critical level $R_{cr}$ (p<0.05) would be 2.73.

Figure 5:
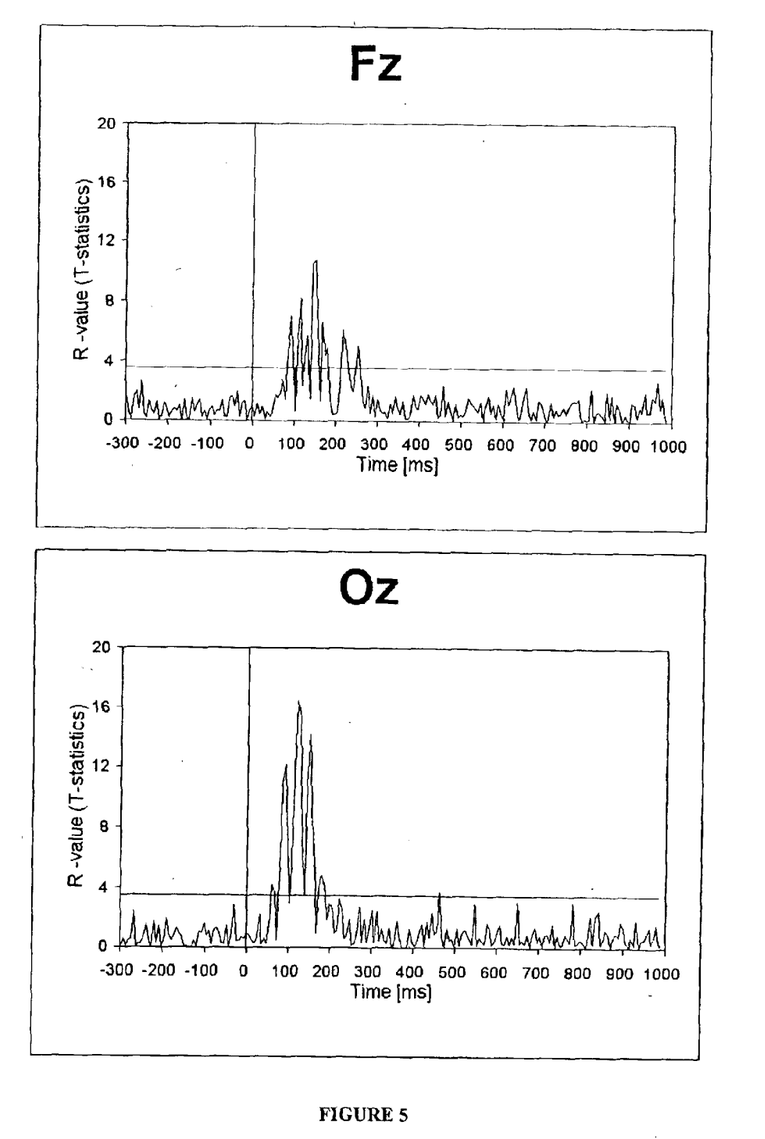

Absolute values of R calculated from the recordings in subject SB are presented in FIG. 5. One can see a significant increase in the R-value in the specific time range (e.g. from 50 to about 300 ms) where the conventional evoked potential is usually obtained. The calculated critical level $R_{cr}$=3.5 is indicated in FIG. 5 as the line parallel to the time axis and cutting the profile of the R-values. The time interval during which the R-values project above the critical level of 3.5 and then below it, can be used to define the period of appearance of evoked activity.

2. Detailed Analysis of Background Activity on the Basis of the Deflection Time Distributions Time Intervals Between Successive Deflections and Rate of Deflections The mean time interval between successive deflections and the reciprocal of this value (termed here rate, or frequency of deflections) is one of the principal characteristics of the background activity and can be estimated in the following way: For example, there were 2–6 positive deflections in each of the 300 ms prestimulus time intervals recorded in subject SB, with a mean across all 300 trials of 4.24±1.07 deflections. A mean number of 4.24 deflections in 300 ms gives a mean rate in subject SB of 14.13±3.56 Hz (range 6.67–20 Hz), and a mean time between successive deflections (period) of 70.8±24.1 ms.

A similar operation was performed on the 300 ms prestimulus periods from all 6 sessions recorded in all 14 subjects. The mean rate across subjects was 15.25±0.78 Hz. Thus the rate of deflections detected in the 300 ms prestimulus period (background activity) in the 14 subjects lies within the beta range of EEG activity (for the Oz electrode).

Figure 6:
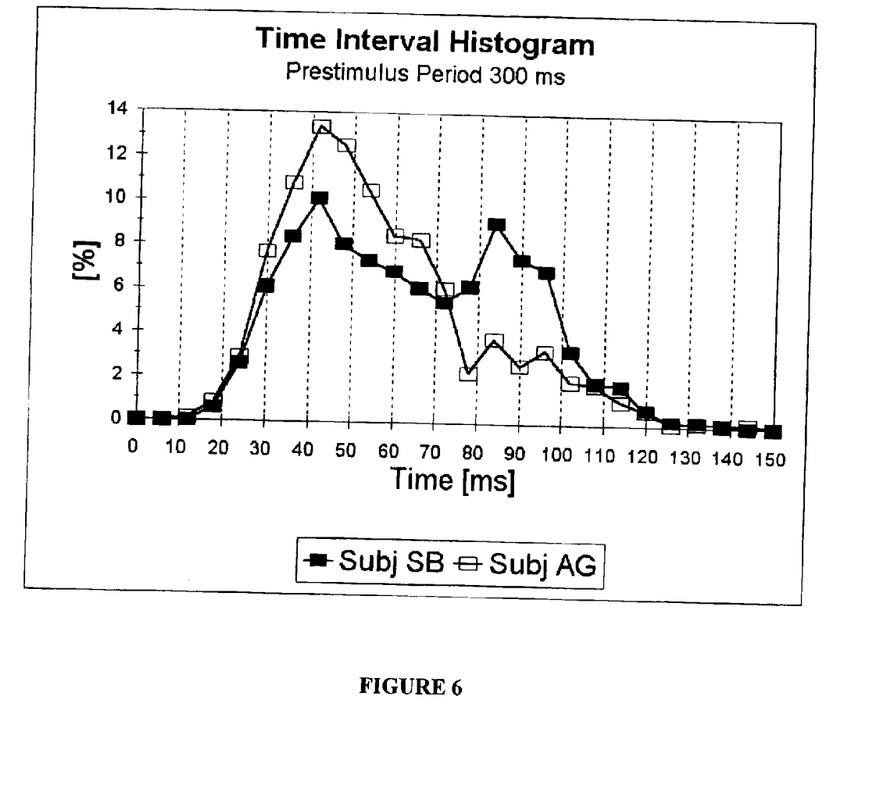

While the mean rate of deflections calculated from the deflection time distribution algorithm is in the beta range, the frequency content of the raw EEG was obviously broader, also containing oscillations lower in frequency. The histograms of the time intervals between the successive positive deflections calculated by our algorithm in the 300 ms prestimulus EEG in 2 subjects was constructed (data over 300 EEG segments, FIG. 6).

The time interval histograms (FIG. 6) show that more than 95% of the positive EEG deflections detected by our algorithm appear with time intervals shorter than 110 ms between successive deflections, i.e. with a rate greater than 9 Hz, mostly in the Alpha and Beta range. The Fourier spectrum of the raw EEG segments from the same data had a much broader frequency content, including lower frequencies.

The relatively high frequency content of the deflections (without low frequencies) used in this analysis is obviously the result of the low pass filtering at 30 Hz and the subject algorithm which detects all peaks and then takes the time interval between successive peaks from which to calculate rate. It therefore concentrates on the highest frequencies present in the raw EEG and does not take into account the broader (lower frequency) content.

a. Characterization of the Overall Evoked Response

The R-values for the description of the background activity (see formula 1) can also be used to define the time range of the onset, termination and duration of the visual evoked activity. These are presented in Table 1 below. The onset of the response at the Oz electrode was significantly earlier probably because this is the region of the primary visual cortex. Duration of the overall responses at these electrodes did not differ significantly.

Table 1 presents data for the whole set of EP-components: N1-P1-N2. However, one can consider each of the components separately since they can be statistically defined as different peaks using the criteria R-value. Moreover, positive and negative components can be presented separately, depending on the sign of the nominator used to calculate the R-value (#p−#n), (formula 1).

TABLE 1

Mean and standard deviations values of the onset, termination, and duration of the overall activity evoked by the visual stimulation in 14 subjects. Time duration of analysis was 1300 ms with a critical $R_{cr}$ value = 3.5. Data from four electrodes.

|  | Oz | Pz | Cz | Fz |
|---|---|---|---|---|
| Onset: [ms] | 60.0 ± 7.9 | 77.5 ± 22.0 | 92.0 ± 16.6 | 87.5 ± 14.9 |
| Termination: [ms] | 214.5 ± 23.4 | 248.0 ± 25.1 | 227.3 ± 20.5 | 234.5 ± 13.7 |
| Duration: [ms] | 154.5 ± 26.7 | 170.5 ± 38.0 | 135.3 ± 27.0 | 147.0 ± 25.5 |

Figure 7:
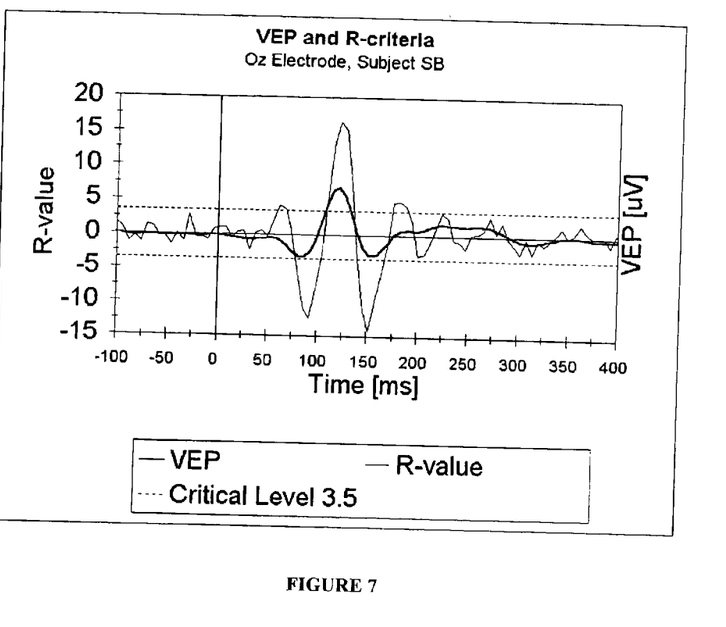
Figure 8A:
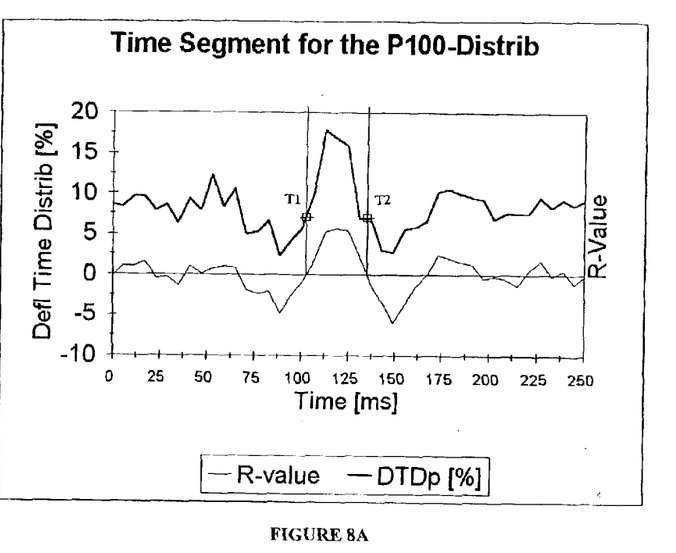

FIG. 7 shows both the R-value definition of evoked activity based on the deflection time distributions and the conventionally averaged VEP from the same data. One can see good agreement between both curves: the principal VEP-components are present in the time regions where the R-value projects above the critical level $R_{cr}$=3.5. Inspection of the R-value definition in FIG. 7 reveals the principal components of VEP (N1, P1, N2) and in addition the possible presence of evoked activity which is not apparent in the conventionally averaged VEP (positive components at 60 ms and 180 ms).

b. Breakdown of the Particular EP-components from the Peaks of Deflection Time Distributions The correspondence between the known components of conventional EP, the deflection time distributions and R-values permits the separation of the overall deflection time distribution of evoked activity into its local distribution for individual EP components. The separation of the positive deflections associated with VEP P1 component from the deflection time distribution obtained in subject SB is illustrated in the FIG. 8A. The goal of this procedure is the determination of the left (T1) and right (T2) borders of the time segment containing time bins with a high percentage of the positive deflections which can be related to VEP P1. The following conditions have to be fulfilled by this procedure:

1) the time segment (T1, T2) has to include the time bin ($T_{peak}$) which corresponds to the latency P1 VEP and contains a peak value of (positive) deflections;
2) the R-value calculated for this time bin ($T_{peak}$) has to exceed the critical level $R_{cr}$;
3) the R-values of the other time bins neighboring the $T_{peak}$ bin and within this segment (T1, T2) have to have the same sign as the R-value of the $T_{peak}$ bin (i.e. to be greater a zero for the distribution of positive deflections);
4) the border bins T1 and T2 may have R-values equal to zero.

Figure 8B:
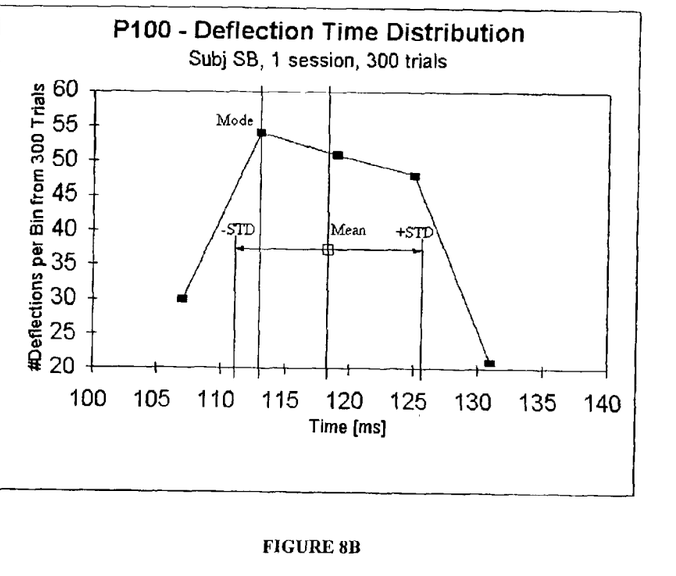

That part of the positive deflection time distribution related to the time bins [T1, T2] was defined as the partial deflection time distribution corresponding to the VEP component P1. The partial deflection time distributions corresponding to VEP components N1, N2 can be described in a similar way. The partial distributions corresponding to the VEP N1, P1, N2 components were determined for the Oz electrode in all 14 subjects. An example of the partial distributions corresponding to the P1 component obtained in the recordings in subject SB (one session, 300 trials; using the procedure presented in FIG. 8A is presented in FIG. 8B. One can see that the time interval [T1, T2] where positive deflections related to the P1 appear, has a duration of 30 ms (5 time bins of 6 ms). Within this time range over 300 trials there were 204 positive deflections not uniformly distributed over these 5 bins, and the maximal number of deflections (54 out of 300 trials) was obtained in the 110–116 ms bin (i.e. $T_{peak}$, the mode of the distribution, was 113 ms).

c. Analysis of the EP-components Variability on the Basis of the Partial Deflection Time Distributions The partial deflection time distributions corresponding to the EP components can be used as a measure of the variability of the evoked response across single trials, this is illustrated in FIG. 8B. The mean latency and standard deviation (s) of these deflections was: 118.3±7.3 ms. The parameter Standard Deviation [ms] may serve as a measure of the "time jitter" of the given EP-component, i.e. trial to trial variability of latency. An additional measure of the variability of the latency of responses may be provided by the possible asymmetry of the partial time distribution of a wave, i.e. if the slopes on either side of the peak differ. In that case the modal latency and the mean latency will differ. For example, in FIG. 8B (subject SB) the time coordinate of the peak number of deflections (mode) $T_{peak}$ is 113 ms and mean value of the latency of the deflections $T_{mean}$ is 118.3 ms. This gives an asymmetry of the partial distribution (as): as=$T_{peak}$−$T_{mean}$=113−118.3=−5.3 ms.

The parameters of the partial time deflection distributions, calculated for VEP-components N1, P1, N2 over 14 subjects by methods described above, are presented hereinafter in Table 2. The calculation of the T1 and T2 for VEP components N1 and P1 (electrode Oz) in all 14 subjects revealed that as a rule, the duration of time interval (T1, T2) for these components is less then 30 ms. Since the time interval between successive deflections of a specific polarity is significantly longer then 30 ms (for example the mean time interval evaluated in background activity over all 14 subjects was 65.6 ms), it is not likely that there can be more then one deflection contribution to the time range of the partial deflection time distribution of N1 or P1 in response to a single stimulus (single trial). In other words, there seems to be a one-to-one correspondence between the deflections which make up the partial time distribution and the trials related to this distribution. The number of trials whose deflections contribute to this distribution is less than the total number of trials used in the analysis (e.g. in FIG. 8B there were only 204 deflections in the P1 time distribution across 300 trials). This means that in some stimulus trials a positive deflection was absent in the P1 time range. The mean percentage of trials containing the "appropriate deflection" can be evaluated from Table 2. For example, a deflection in the P1 component time range was present in our subjects in approximately 224.7 trials out of 300, i.e. in 75% of the trials. These trials containing "appropriate" deflections can be considered as an approach to single trial analysis.

TABLE 2

Parameters of VEP-components in Partial deflection time distributions:

| | N1 | P1 | N2 |
|---|---|---|---|
| Peak Value of the partial distribution: [%] # deflection/300 | 18.9 ± 4.4 | 22.1 ± 4.9 | 15.3 ± 3.3 |
| Latency of the peak number of deflections: $T_{peak}$ [ms] | 88.8 ± 8.7 | 121.0 ± 4.4 | 157.0 ± 11.0 |
| T1 [ms]: Left border of the partial distribution | 80.4 ± 8.0 | 108.3 ± 5.3 | 140.9 ± 9.3 |
| T2 [ms]: Right border of the partial distribution | 101.4 ± 6.7 | 132.7 ± 4.6 | 180.3 ± 17.6 |
| Width (duration) of the partial distribution T2 − T1 [ms] | 21.0 ± 3.0 | 24.4 ± 4.8 | 39.4 ± 13.6 |
| Mean Latency of deflections contributed to the partial distribution $T_{mean}$ [ms] | 90.2 ± 7.1 | 120.2 ± 4.6 | 156.5 ± 12.8 |
| Standard Deviation of the latency of deflections contributed to the partial distribution: s [ms] | 6.9 ± 0.8 | 7.5 ± 1.3 | 9.4 ± 2.6 |
| Asymmetry of the partial distribution [ms] $T_{mode} - T_{mean}$ | −1.4 ± 2.8 | 0.8 ± 3.2 | 0.5 ± 14.7 |
| Mean # Deflections contributed to the partial distribution (from 300 trials) | 186.3 ± 30.2 | 224.7 ± 35.4 | 236.5 ± 70.2 |

Mean ± SD in 14 subjects. Electrode Oz.

d. Application of the Deflection Time Distributions (R-criteria) for Response Determination The clear correspondence between the time distributions of deflections detected by the algorithm used here and the components of the conventional averaged EP with respect to N1 and P1 leads to the suggestion that these principal components of the VEP are generated by the EEG deflections themselves. During background EEG, the deflections are dispersed randomly in time, at a rate of about 15 Hz, as shown. Upon repeated stimulus presentations (trials) there is a tendency for the deflections to appear within narrow time periods after the stimulus. That is, when examining these periods following repeated stimulus trials, there is a "synchronization" of the deflections over many, but not all, stimulus trials.

Synchronization (time-locking) of deflections is reflected in the relative number of positive and negative deflections obtained in the time bins, and the R-value (formula 1) has been applied in order to separate between background and evoked activity. A high R-value is produced in a particular time bin when this bin contains more deflections with a specific polarity than some criterion. This means that a deflection of that polarity (positive or negative) was generated in the given time bin in many trials, while the opposite polarity deflections appeared only rarely. Thus a significantly high R-value in the particular bin, or for the set of bins (i.e. for the some time interval),—is an indication of synchronization (time-locking) of the deflections of that polarity in response to the stimulus. This measure of synchronization (high magnitude of R) is exclusively dependent on the presence of the deflections and not on their amplitude. Therefore the correspondence between VEP parameters and R-value provide evidence for the important role of synchronization of deflections in producing the conventionally averaged EP.

Thus it is proposed that the N1 and P1 components of the VEP were produced by the time locking of EEG deflections (synchronization in response to the successive stimuli) probably those in the high alpha—and beta range (7–30 Hz). These deflections can be considered as the single stimulus trial responses which contribute to the final averaged response. This suggestion for generation of the VEP components may not be appropriate for component N2 because it seems that its duration (time interval of the corresponding partial deflection distribution) is greater than 30 ms and there may be more than one deflection in this time range.

3. Amplitude of Deflections and the Amplitude Profile in Background Activity

Figure 9:
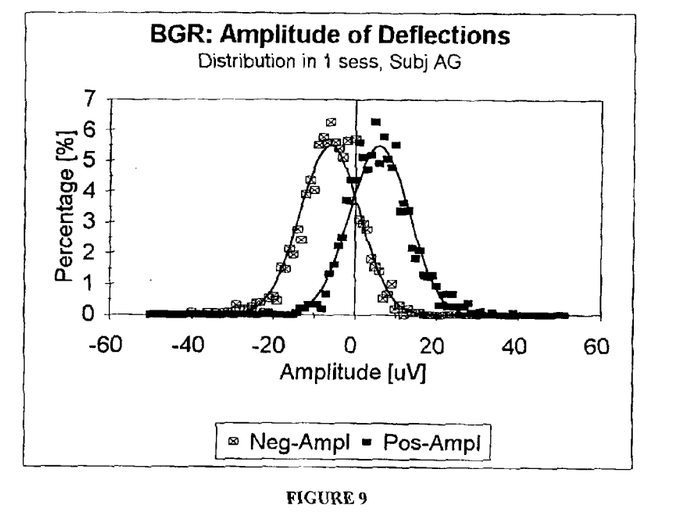

Due to the stationarity of background activity, the data obtained over periods of background activity can be combined. In order to illustrate the amplitudes and. variation of the amplitude of the EEG deflections measured during background activity, the amplitudes of the deflections in the 300 ms prestimulus periods in 300 trials in one session for subject AG were calculated. The mean (±SD) amplitude of the positive deflections was 6.06±7.28 uV (n=1483 deflections) and for the negative deflections was −6.05±7.24 uV (n=1482). FIG. 9 shows the distribution of their amplitudes. The two distributions (positive and negative deflections) are very similar as expected, since, by definition, during background activity the EEG is symmetrical both with respect to the rate of deflections (see R-value, described above) and their amplitude. These amplitude distributions could be approximated by a normal (Gaussian) variance symmetrically around the mean, with identical SDs for both positive and negative deflections (see FIG. 9). The distributions of the amplitude of deflections during background activity differed in different subjects: the means ranged from 2 to 8 uV over the 14 subjects, with a mean amplitude over all subjects of 4.73±1.80 uV for the positive deflections, and −5.03±1.70 uV for negative deflections (n=14).

Such mean value of the amplitude of the "background" deflections (positive or negative) presents a level around that the mean amplitudes calculated for the deflections which contributed to the given (successive) time bins (i.e. values of the Amplitude Profile), fluctuate (FIG. 3 for example). One can note that these fluctuations are much smaller than deviation of the amplitude of the single deflections, since the values of Amplitude Profiles are the product of averaging. For example, the fluctuations of the amplitude of the positive EEG deflections calculated without averaging in time bins across trials were evaluated in subject SB over 6 sessions as 6.48±6.91 uV, and at the same time the values of the Amplitude Profiles (calculated over 6 sessions) fluctuated as 6.48±0.55 uV.

4. Differentiation Between Background and Evoked Activity on the Basis of the Peak Amplitude of Deflections The variation of the values of the Amplitude Profile for the time period of background activity in a given subject may be used to generate a statistical criteria for the determination of significant amplitude deviations which could serve as a sign of evoked activity (similar to the criteria used to differentiate between background and evoked activity based on the deflection time distributions.

For example, in subject SB the mean and standard deviation of the amplitude of the deflections during background activity over 6 sessions was 6.48±0.55 uV for positive deflections and −6.52±0.53 uV for negative. By how much should amplitudes have to differ from this mean in order to be considered to have surpassed it and therefore defined as evoked activity; i.e. what is the criterion magnitude of this critical deviation?

Figure 10:
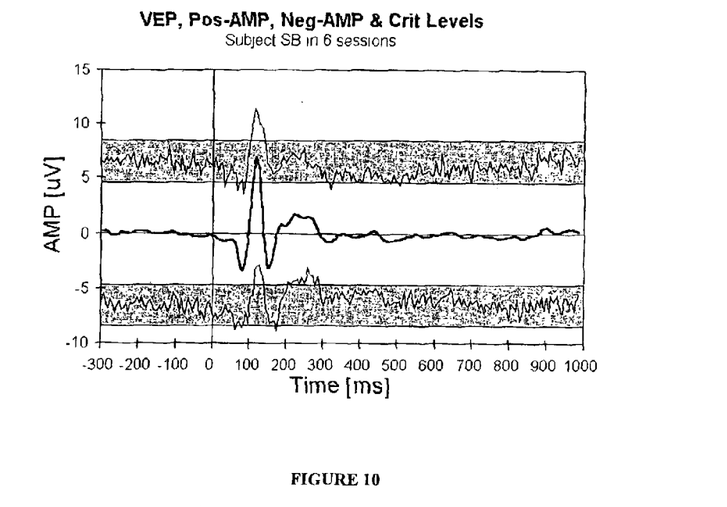

As noted above a significance of p<0.05 may be achieved in our case if one uses a criteria of ±3.5 SDs from the mean value obtained during background activity. Thus, with respect to subject SB, the critical value for positive deflections is 8.40 uV (6.48+3.5×0.55), and for negative deflections −8.38 uV. (In addition the criteria for determination of amplitudes significantly lower than background can also be calculated: for positive deflections=4.56 uV, for negative=−4.66 uV). These criteria for the positive and negative deflections are indicated in FIG. 10 as the shaded area. The Amplitude Profiles reach and project above these critical levels during the time regions corresponding to the evoked components, and this seems to be clearer for the positive waves.

This leads to the suggestion that there are two different mechanisms of response generation acting in different subjects in different proportions: first, one responsible for the occurrence of the wave (the peak of neuronal activity, EEG-deflection) at a certain moment after the onset of the stimulus (latency), and the second one, responsible for its magnitude. Thus, appearance of a peak (component) in the conventional averaged EP in response to repeated stimuli is probably determined by two factors: (1) the synchronization of the deflections (the time locking of deflections) and (2) an increase in the amplitude of these deflections, (i.e. the amplitude of the deflections during the specific period is greater than that during background activity). The second one can be called "amplification" of deflections and it is really due to the enhanced synchronization of synaptic-dendritic potentials initiated by stimuli.

5. Correlation Between the Mean Amplitude of Deflections Corresponding to the EP Components and the EEG Deflections in Background Activity There was a strong positive correlation between the peak value of the Amplitude Profiles corresponding to the N1 and P1 components and the mean amplitude of deflections in the background activity at the parietal and occipital scalp electrodes (Pz,P3,P4, Oz,O1,O2,T5,T6) where response (conventional VEP) was maximal, and at the central electrodes (Cz,C3,C4). This, it seems, that subjects with larger amplitudes of deflections during background activity also had larger amplitudes of their N1 and P1 VEPs. The parameters of this dependence (correlation coefficient, slope of regression line and intercept) differed slightly between N1 and P1 components and were different on electrode. The correlation coefficient ranged for N1-component from 0.879 (Oz) to 0.983 (P4), and for P1-component from 0.690 (Oz) to 0.914 (P4). The slope of regression line was maximal on the occipital electrodes (Oz,O1,O2): these occipital values ranged from 1.38 to 1.23 for N1, and from 1.77 to 1.49 for P1-component.

The results of this part of the study on the interrelations between evoked and background activity leads to the suggestion that different components of the EP might be differently related to and originating from the background activity.

The method of the present invention offers a number of advantages over prior methods of analysis of EEG generated data, as follows:

1. It provides a form of single trial analysis with a greater degree of distinction between ongoing cortical electrical activity and evoked cortical electrical activity.
2. It allows individual analysis of both the timing and the amplitude of deflections, the two mechanisms involved in generation of the conventionally averaged EEG data for evoked responses.
3. It provides insight into possible mechanisms involved in the generation of evoked cortical electrical activity based on the time-locking (EEG-synchronization) and amplitude amplification of EEG deflections.
4. It allows detailed evaluation of the temporal properties of EP activity using methods similar to the study of trains of spikes (for example, analogous to post-stimulus time histograms—deflection time distributions and time interval histograms which were used in the present study).
5. It allows study of correlation between the time structure of the occurrence of deflections and their amplitude.

In summary, the method of the present invention allows for detailed analysis of background and evoked EEG data within different frequency ranges, providing information about the stimulus evoking the response. Such analysis may be useful in the evaluation of cortical electrical activity in clinical cases.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

It will be appreciated by persons skilled in the art that the present invention is not limited to what has been particularly shown and described hereinabove. Rather, the scope of the present invention is defined by the appended claims and includes both combinations and subcombinations of the various features described hereinabove as well as variations and modifications thereof which would occur to persons skilled in the art upon reading the foregoing description. Accordingly, it is intended to embrace all such alternatives, modifications and variations that fall within the spirit and broad scope of the appended claims.

What is claimed is:

1. A method of analyzing EEG data in order to differentiate between ongoing neuro-electric activity of the brain of a subject and evoked neuro-electric activity of the brain of said subject, said analysis being based upon the time, polarity and amplitude distributions of deflections from the base line of said EEG and EP data, said method comprising a. recording by EEG measurement said ongoing neuro-electric activity;
    b. administering a series of sensory stimuli to said subject;
    c. recording by EEG and EP measurement neuro-electric activity evoked in response to said stimuli;
    d. marking the time of occurrence, polarity and amplitude of each of said deflections recorded;
    e. generating a histogram of time periods of said deflections for a defined duration prior to, during and subsequent to each of said stimuli, said histogram reflecting the deflections within said time periods, generating a deflection time distribution based upon data from said histogram, generating an amplitude profile of said deflections; and
    f. using said deflection time distribution and said amplitude profile to statistically analyze and evaluate the ongoing and evoked neuro-electric activity, such that the differentiation between said ongoing neuro-electric activity and said evoked neuro-electric activity may be quantified.

2. The method of claim 1, wherein said method is modifiable to allow quantification of evoked neuro-electric activity of different frequencies and amplitudes.

3. The method of claim 1, further comprising identifying at least one of said stimuli evoking said neuro-electric activity.

4. The method of claim 1, further comprising analyzing at least one of said stimuli evoking said neuro-electric activity, and examining said evoked neuro-electric activity, said examination including one or more of the group consisting of the timing of said neuro-electric activity; the variability of said neuro-electric activity; and the correlation of said neuro-electric activity.

5. The method of claim 1, wherein said stimuli are sensory stimuli.

6. The method of claim 5, wherein said sensory stimuli are visual stimuli.

7. The method of claim 1, wherein said stimuli include performing an attention demanding task.

8. The method of claim 1, wherein said stimuli include engaging the memory process.

9. The method of claim 1, wherein said time periods range between 3 ms and 10 ms.

10. The method of claim 1, wherein said time period is 6 ms.

11. The method of claim 1, wherein said deflections are both positive and negative deflections.

12. The method of claim 1, wherein said method is actuatable and operatable by a computer.

13. The method of claim 1, including using the method to measure the effect of said stimuli on said subject compared to the effect of said stimuli on other subjects.

14. The method of claim 1, including using the method to measure the effect of said stimuli on said subject over a period of time.

15. The method of claim 1, including using the method to measure the effect of medicine on a response of said subject to said stimuli.

16. The method of claim 1, including using the method to measure the effectiveness of a remedial program on a response of said subject to said stimuli.

17. The method of claim 1, including using the method to measure the effect of fatigue on a response of said subject to said stimuli.

18. The method of claim 1, including using the method to measure the effect of injury or disease on a response of said subject to said stimuli.

19. The method of claim 1, including using the method to measure the effect of recovery from injury or disease on a response of said subject to said stimuli.

* * * * *